United States Patent [19]

Hietala

[11] 4,062,226
[45] Dec. 13, 1977

[54] DEVICE FOR MEASURING PULP STOCK CONSISTENCY

[75] Inventor: Veijo Hietala, Tampere, Finland

[73] Assignee: Valmet Oy, Finland

[21] Appl. No.: 677,060

[22] Filed: Apr. 14, 1976

[30] Foreign Application Priority Data

Apr. 18, 1975 Finland .................................. 751172

[51] Int. Cl.$^2$ ........................................... G01N 11/00
[52] U.S. Cl. ........................................................ 73/63
[58] Field of Search .................... 73/63, 61 R, 59, 228

[56] References Cited

U.S. PATENT DOCUMENTS

| | | | |
|---|---|---|---|
| 1,125,017 | 1/1915 | Green | 73/59 |
| 2,917,922 | 12/1959 | Morse | 73/228 |
| 3,364,730 | 1/1968 | Wall | 73/59 |

FOREIGN PATENT DOCUMENTS

300,559  7/1971  U.S.S.R. .................................. 73/63

Primary Examiner—Richard C. Queisser
Assistant Examiner—Joseph W. Roskos
Attorney, Agent, or Firm—Steinberg & Blake

[57] ABSTRACT

A device for measuring the consistency of pulp stock flowing in a given direction along a conduit. The device includes a carrier shaft which extends transversely with respect to the direction of stock flow, and this carrier shaft carries a sensing element extending from the carrier shaft in the downstream direction of stock flow into the stock for shearing the flowing stock and for responding to engagement with the stock for producing a torque capable of being measured for indicating consistency of the stock. A supporting structure supports the carrier shaft and the sensing element carried thereby for adjustable angular movement about an axis which is perpendicular to the carrier shaft and which also extends transversely with respect to the direction of stock flow, the sensing element having a surface situated in a plane which is oblique with respect to the latter axis and with respect to the carrier shaft, so that depending upon the direction and angle of adjustment of the carrier shaft and sensing element carried thereby with respect to a neutral position where the oblique surface extends in the direction of stock flow, the stock will be deflected by the oblique surface to a given extent in a given direction producing in this way a torque of a direction and magnitude which depends upon the velocity of stock flow, with respect to the carrier shaft and sensing element.

7 Claims, 8 Drawing Figures

DEVICE FOR MEASURING PULP STOCK CONSISTENCY

BACKGROUND OF THE INVENTION

The present invention relates to a pulp stock consistency measuring device adapted to be used in a paper manufacturing machine, for example, where it is important to provide in the headbox a pulp stock of a predetermined consistency.

In particular, the present invention relates to a pulp stock consistency measuring device which is adapted to be situated in a conduit along which the stock flows with a sensing member of the device shearing the flowing pulp stock while reacting in response to engagement therewith for providing a torque which can be measured for indicating the consistency of the stock.

In accordance with the measurement of the consistency of the flowing pulp stock suitable controls will be actuated for adding to the stock a suitable diluting solution in the event that the consistency measurement indicates that the stock is too thick, or reducing the amount of diluting solution which is added to the stock in the case where the consistency measurement indicates that the pulp stock consistency is not great enough.

One of the problems encountered with consistency measuring devices of this type is that the torque measurement is undesirably affected by variations in the velocity of flow of the pulp stock, so that these variations resulting from the pulp stock velocity flow introduce errors in the measurement of the consistency of the stock.

In the paper and cardboard industry measuring devices of this type are used among others for measuring the consistency of the pulp stock, such devices being mounted in a conduit or pipe through which the stock flows and including a sensing means which shears the flowing stock. The torque actuated by the sensing means as a result of engagement between the sensing means and the flowing pulp stock serves as a basis for the consistency measurement. With respect to the state of the art reference may be made, for example, to Finnish Pat. No. 33,814. As has been indicated above, one of the problems encountered with measuring devices of this type is that the variations in the flow velocity of the pulp stock undesirably affect the results of the measurement. Attempts have been made to compensate for these effects, for example in the manner disclosed in Finnish Pat. No. 41,695.

Thus, it has been attempted in measuring devices of this type to give the sensing element a configuration according to which the extent to which the measured torque depends upon the flow velocity of the pulp stock is minimized. Thus, with this latter objective in mind the sensing element conventionally has been given the shape of a suitably curved paddle, with the paddle extending in the downstream direction with respect to the flowing stock. The plane of the blade of the paddle is conventionally perpendicular to a shaft which carries the sensing member, and a measuring mechanism measures the torque produced with respect to this shaft. By selecting in advance a suitable magnitude of the angle between the paddle blade and the direction of flow in a plane at right angles to the shaft which carries the blade, or by joining to the blade surfaces which deflect the flowing stock, it has been possible to provide a torque which is substantially independent of the flow velocity within a given flow velocity range, but this latter limited result has been achieved only with a given range of stock consistency, so that desired results can only be achieved in a manner which is dependent upon the type of fibers which are in the stock.

SUMMARY OF THE INVENTION

It is accordingly a primary object of the present invention to provide a consistency measuring device of the above type which not only can provide a torque which is independent of the flow velocity of the pulp stock but which also is capable of achieving this result in a number of different ranges of consistency of the stock, so that reliable consistency measurement can be achieved even with different pulp stocks of considerably different consistencies.

It is also an object of the present invention to provide a stock measuring device which can achieve these results with an exceedingly simple structure which operates in a new and unexpected manner to enable the desired results to be achieved.

A more particular object of the present invention is to provide a construction which can easily be adjusted for achieving the desired results with different types of pulp stock.

According to the invention the pulp stock consistency measuring device includes a carrier shaft means which extends transversely with respect to the direction of stock flow and which carries a sensing means which extends downstream from the carrier shaft means while being situated in the stock to shear the latter and produce a torque in response to engagement with the stock. According to the invention a support means supports the carrier shaft means and sensing means for angular adjustment about an axis which is perpendicular to the carrier shaft means and which also extends transversely with respect to the direction of stock flow, with the sensing means itself having, according to a further feature of the invention, a surface situated in a plane which is oblique with respect to the carrier shaft and the axis around which the adjustment is made.

Thus, when the sensing means is turned by way of the adjustable support means with respect to the latter axis to a given extent and in a given direction with respect to a neutral position where the oblique surface extends in the direction of stock flow, the stock flow will be deflected in a given direction and by a given magnitude by the oblique surface thus achieving torque of a given direction and magnitude depending upon the flow velocity of the stock, with respect to the carrier shaft means and sensing means carried thereby.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
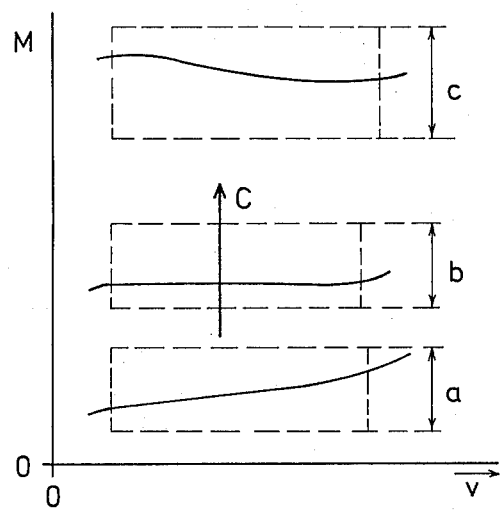
FIG. 1 is a graph schematically representing the torque of a sensing means as a function of flow velocity of the pulp stock at different consistencies of the stock.

Referring first to FIG. 1, the set of curves illustrated therein show the torque M of a sensing member as a function of the flow velocity $v$ of the pulp stock, with different consistencies C and with a given type of fiber. Thus, at the intermediate consistency range $b$, the influence of the flow velocity $v$ is negligible. However, in the consistency range $a$ a more pronounced compensation for the effect of the flow velocity $v$ would be required than in the consistency range $b$. In the consistency range $c$, the compensation for the effect of flow of velocity $v$ need not be as pronounced as in the case of consistency range $a$, and also the compensation would be in a direction different from that of the consistency range $a$.

Figures 2A, 2B:
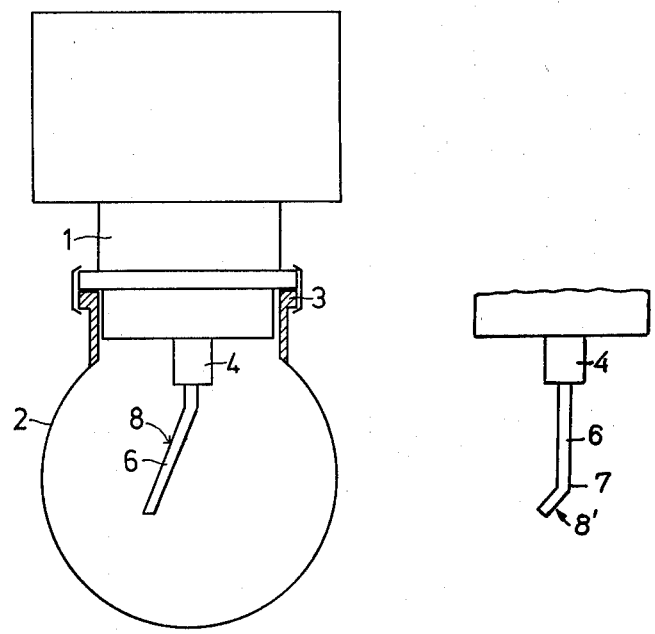
FIG. 2A illustrates one embodiment of a pulp stock consistency measuring device of the invention, FIG. 2A being partly in section and schematically showing the device as it appears when viewed in the direction of stock flow, the plane of FIG. 2A being transverse to the direction of stock flow.
FIG. 2B fragmentarily illustrates another embodiment of a device which is similar to that of FIG. 2A.
Figure 3:
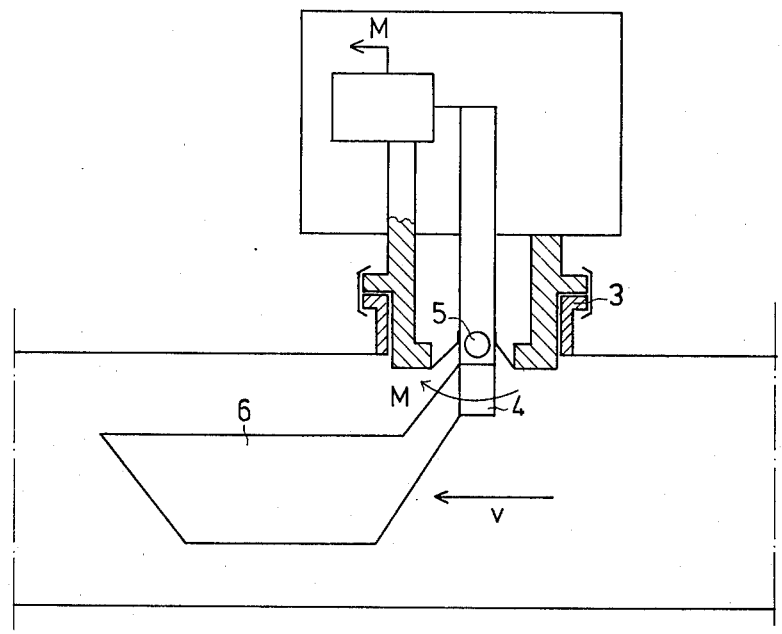
FIG. 3 schematically represents the structure of FIG. 2A in a longitudinal elevation taken in a plane which is in the direction of stock flow.
Figure 4:
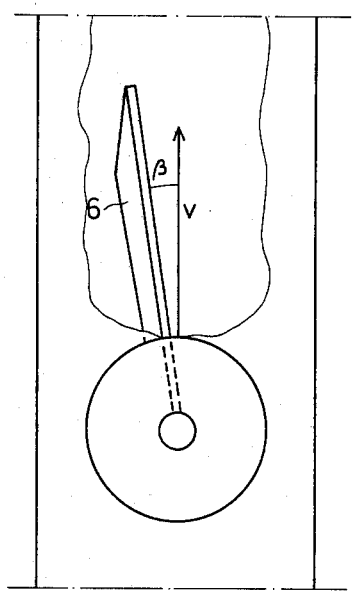
FIG. 4 is a schematic plan view showing how the embodiment of FIGS. 2A and 3 is adjusted.

The embodiment of the invention which is illustrated in FIGS. 2A, FIG. 3, and FIG. 4 provides a solution to the above problems according to which it becomes extremely easy to provide in the measuring device a regulation which will compensate for the pulp stock flow velocity. The measuring device 1 is connected with a conduit means 2 in the form of a suitable pipe or tube along which the pulp stock flows. For this purpose the conduit means 2 includes a support means 3 for supporting the measuring device 1 for turning movement about an axis which extends transversely with respect to the direction of stock flow, this axis being vertical in FIGS. 2A and 3 while being normal to the plane of FIG. 4. As is apparent from FIGS. 2A and 3, the support means 3 is in the form of a circular tubular extension of the conduit means 2, so that the support means 3 is of a cylindrical configuration and is circular in cross section. The device 1 has a portion extending freely through the tubular support means 3 and includes a flange which engages the upper surface of the support means 3, as viewed in FIGS. 2A and 3, so that in this way the entire device 1 is capable of being turned with respect to the conduit means 2 about the axis of the cylindrical support means 3. Any suitable exterior clamp is provided for releasably clamping the device 1 to the support means 3 and thus to the conduit means 2 in an adjusted angular position. The measuring device 1 includes a sensing means 4 so that this sensing means 4 turns with the entire measuring device 1 about the axis of the support means 3 when an adjustment is made as described in greater detail below.

The sensing means 4 is carried by a carrier shaft means 5 which is perpendicular to the axis provided by way of the support means 3 and which also extends transversely with respect to the direction of flow, indicated by the arrow $v$ in FIG. 3. Thus, the flowing stock in the conduit means 2 will tend to turn the sensing means 4 about the axis of the carrier shaft means 5 so that through the latter carrier shaft means 5 it is possible to obtain a torque value M as indicated schematically in FIG. 3 from the device, this torque being used to control the consistency in a well known manner. The sensing means 4 is directly carried by the shaft 5 which in turn is journalled in the body of the measuring device 1 so that through the shaft 5 the sensing means 4 is journalled in the body of the measuring device.

The sensing means 4 includes an elongated blade 6 having the configuration of a paddle and shown most clearly in FIG. 3 from which it is apparent that the blade 6 of the sensing means 4 extends into the body of the flowing stock in a downstream direction from the carrier shaft means 5. In conventional constructions the element which corresponds to the blade or paddle 6 is situated in a plane which contains the axis of the support means 3 around which the device 1 is moved for the purpose of providing an angular compensating adjustment. However, according to the present invention, instead of the blade being situated in such a plane it is inclined with respect thereto so that the blade 6 has the oblique position indicated most clearly in FIG. 2A.

Thus, as is apparent from FIG. 2A, the blade 6 is situated in a plane which is oblique with respect to the carrier shaft means 5 and the axis about which the device 1 can be angularly adjusted. In conventional constructions the blade 6 is situated in a plane which contains the axis about which the angular adjustment is made.

Thus, with the structure of the present invention when the adjusting device is in the so-called neutral position where the blade 6 extends in the direction of flow of the stock, the adjusting device of the present invention is very similar to the previously known devices and operates in a similar way. However, as may be seen from FIG. 4, where the direction of flow is indicated by the arrow $v$, it is possible to adjust the device about the axis of the support means 3 through an angle such as the angle $\beta$ shown in FIG. 4. Now the blade 6 will introduce a change in the direction of flow which in turn gives rise to a force which acts on the blade 6 at right angles to its surface this force being proportional to the square of the flow velocity of the pulp stock. This force produces with reference to the carrier shaft means 5 of the sensing means a torque the magnitude of which is proportional to the square of the flow velocity. The coefficient of proportionality in its turn is dependent, including its sign, on the magnitude of the angle $\beta$. It is thus possible by varying this angle $\beta$ to select that compensation which is most appropriate in view of the particular type of fiber and stock consistency range, this compensation being determined either by experimentation or on the basis of empirical data which has been otherwise obtained. With such a selection in mind, the measuring device 1 can be provided with an adjusting scale which is not illustrated and from which the angle $\beta$ can be read.

In the embodiment of the invention which is illustrated in FIG. 2B, the blade 6 is angled at 7 to achieve the surface which is in the oblique plane. Thus in FIG. 2A the blade 6 has the oblique surface 8 which is the surface of the entire blade, whereas in FIG. 2B, at least one elongated edge region of the blade has been angled at 7 to provide the oblique surface 8', so that in this embodiment the blade 6 is only partially in the oblique plane. Of course if desired, the opposed upper and lower edge regions of the blade 6 may be provided with the oblique edge regions, although only one is illustrated in FIG. 2B.

Figure 5A:
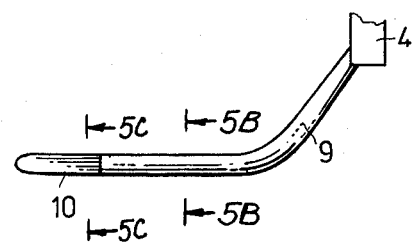
FIG. 5A is an elevation of another embodiment of the device.
Figure 5B:
FIGS. 5B and 5C are respectively transverse sections of the embodiment of FIG. 5A taken along lines 5B—5B and 5C—5C of FIG. 5A in the directions of the arrows.
Figure 5C:
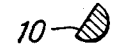

In the embodiment of FIGS. 5A—5C, a further advantageous construction is provided according to which the sensing means 4 which shears the flowing stock is in the form of a rod 9. While the rod 9 is for the most part of a circular cross section, as indicated in FIG. 5B, as is shown in FIG. 5C, a portion of the rod 9 has the oblique flat surface 10 so that the plane of this oblique surface which is thus oblique with respect to the axis of adjustment and the carrier shaft means 5 will also achieve the above-described results of the invention.

Of course, only a few advantageous embodiments of the invention have been presented above. It will be obvious to those skilled in the art that numerous modifications of these embodiments are possible in the spirit of the basic idea of the present invention, without departure from the protective scope of the invention. It is only essential that the torque can be made independent of the flow velocity of the pulp stock, regardless of the consistency range, in the manner taught by the present invention.

What is claimed is:

1. In a device for measuring the consistency of pulp stock flowing in a given direction along the interior of a conduit means, carrier shaft means extending transversely with respect to the direction of flow of stock in said conduit means, sensing means carried by said carrier shaft means and extending therefrom into the stock in said conduit means in the downstream direction of stock flow from said carrier shaft means for shearing the flowing pulp stock and for producing in response to engagement with the flowing pulp stock a torque capable of being measured for indicating the consistency of the pulp stock, and support means supporting said carrier shaft means and sensing means carried thereby for adjustable angular movement to a selected position about an axis perpendicular to said carrier shaft means and also extending transversely with respect to the direction of stock flow, said sensing means having a surface in a plane which is oblique with respect to said carrier shaft means and axis for deflecting the flowing stock in a manner depending upon the extent and direction of angular adjustment of said carrier shaft means and sensing means with respect to said axis from a neutral position where said oblique surface extends in the direction of flow of the stock, so that depending upon the angle of adjustment with respect to said axis the deflection of flow provided by said oblique surface will provide a torque of a given direction and magnitude depending upon the velocity of flow of the stock, with respect to said carrier shaft means and sensing means.

2. The combination of claim 1 and wherein said sensing means is in the form of an elongated paddle having a blade extending downstream with respect to said carrier shaft means, and said blade being situated at least in part in said oblique plane to provide said oblique surface.

3. The combination of claim 2 and wherein said paddle is substantially entirely situated in said oblique plane.

4. The combination of claim 2 and wherein said paddle is for the most part situated in a plane which contains said axis but has at least one elongated edge region situated in said oblique plane.

5. The combination of claim 4 and wherein said blade has only one elongated edge region situated in said oblique plane.

6. The combination of claim 1 and wherein said sensing means includes an elongated rod having at least in part a curved configuration for extending downstream in the flowing stock.

7. The combination of claim 6 and wherein said rod has a flat surface portion situated in said oblique plane.

* * * * *